(12) United States Patent (10) Patent No.: US 8,933,117 B2
Ohkawa et al. (45) Date of Patent: Jan. 13, 2015

(54) CRYSTALS OF SUBSTITUTED CYCLOALKENE DERIVATIVES

(75) Inventors: Nobuyuki Ohkawa, Tokyo (JP); Kouki Iida, Tokyo (JP); Takayoshi Nagasaki, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/825,875

(22) PCT Filed: Sep. 22, 2011

(86) PCT No.: PCT/JP2011/071557
§ 371 (c)(1),
(2), (4) Date: Mar. 25, 2013

(87) PCT Pub. No.: WO2012/039447
PCT Pub. Date: Mar. 29, 2012

(65) Prior Publication Data
US 2013/0178521 A1 Jul. 11, 2013
US 2014/0073689 A9 Mar. 13, 2014

(30) Foreign Application Priority Data

Sep. 24, 2010 (JP) .................................. 2010-213236

(51) Int. Cl.
*A01N 43/26* (2006.01)
*A61K 31/355* (2006.01)
*C07D 317/72* (2006.01)
*A61K 31/357* (2006.01)

(52) U.S. Cl.
CPC ............ *C07D 317/72* (2013.01); *A61K 31/357* (2013.01)
USPC .......................................... 514/467; 549/342

(58) Field of Classification Search
None
See application file for complete search history.

(56) References Cited

U.S. PATENT DOCUMENTS 6,495,604 B1 12/2002 Ichimori et al.
7,935,835 B2 5/2011 Kimura et al.
RE43,858 E 12/2012 Kimura et al.
2006/0058288 A1 3/2006 Ii et al.
2009/0233952 A1* 9/2009 Kimura et al. ................. 514/278

FOREIGN PATENT DOCUMENTS

JP 2000-178246 A 6/2000
JP 2004-2370 A 1/2004
WO WO 00/41698 7/2000
WO WO 2007/032262 A1 3/2007

OTHER PUBLICATIONS

Mullin (Cyrstallization, 2001, 4th Edition, Reed Educational and Professional Publishing).*
Beutler, "Inferences, questions and possibilities in Toll-like receptor signalling," *Nature*, vol. 430, pp. 257-263 (2004).
Cook et al., "Toll-like receptors in the pathogenesis of human disease," *Nature Immunology*, vol. 5, No. 10, pp. 975-979 (2004).
Hawkins et al., "Inhibition of Endotoxin Response by Synthetic TLR4 Antagonists," *Current Topics in Medicinal Chemistry*, vol. 4, pp. 1147-1171 (2004).
Iqbal et al., "Antithrombotic agents in the treatment of severe sepsis," *Expert Opinion Emerging Drugs*, vol. 7, No. 1, pp. 111-139 (2002).
Kakutani et al., "JTE-607, a novel inflammatory cytokine synthesis inhibitor without immunosuppression, protects from endotoxin shock in mice," *Inflammation Research*, vol. 48, pp. 461-468 (1999).

* cited by examiner

*Primary Examiner* — Anna Pagonakis
*Assistant Examiner* — Daniel M Podgorski
(74) *Attorney, Agent, or Firm* — Dorsey and Whitney LLP

(57) ABSTRACT

To provide potassium salts of substituted cycloalkene derivatives, which suppress the production of an inflammatory mediator caused by intracellular signal transduction or cell activation induced by endotoxin, and crystals thereof. The present invention provides potassium (2-chloro-4-fluorophenyl){[(2R,3R,8R)-7-(ethoxycarbonyl)-2,3-bis(hydroxymethyl)-1,4-dioxaspiro[4.5]deca-6-en-8-yl]sulfonyl}azanide and potassium (2-bromo-4-fluorophenyl){[(2R,3R,8R)-7-(ethoxycarbonyl)-2,3-bis(hydroxymethyl)-1,4-dioxaspiro[4.5]deca-6-en-8-yl]sulfonyl}azanide, each of which suppresses the production of an inflammatory mediator caused by intracellular signal transduction or cell activation induced by endotoxin, crystals thereof, and a pharmaceutical containing any of the same, and a prophylactic and/or therapeutic agent for sepsis containing any of the same.

5 Claims, 5 Drawing Sheets

CRYSTALS OF SUBSTITUTED CYCLOALKENE DERIVATIVES

This application is a national stage application under 35 U.S.C. §371 of International Application No. PCT/JP2011/071557, filed Sep. 22, 2011, entitled "Crystals of Substituted Cycloalkene Derivatives," which claims priority to Japanese Patent Application No. 2010-213236, filed Sep. 24, 2010, the contents of all of which are hereby incorporated in their entirety by reference.

TECHNICAL FIELD

The present invention relates to crystals of substituted cycloalkene derivatives, which have activity to suppress intracellular signal transduction or cell activation in various cells such as monocytes, macrophages, and vascular endothelial cells induced by endotoxin, and to suppress the production of an inflammatory mediator such as TNF-α caused by the intracellular signal transduction or cell activation, and which are useful as a prophylactic and/or therapeutic agent for various diseases such as sepsis (septic shock, disseminated intravascular coagulation, multiple organ failure, etc.).

BACKGROUND ART

Endotoxin (lipopolysaccharide: LPS), which is a membrane component of bacteria, acts on cells such as monocytes, macrophages, and vascular endothelial cells, induces the overproduction of various inflammatory mediators such as TNF-α and the like, causes sudden hypotension, blood coagulation disorders, circulatory disturbances, and the like in addition to systemic inflammatory responses, and thus develops sepsis (see, for example, Non-patent document 2). Lipopolysaccharide and Lipid A, which corresponds to a partial structure thereof, activate intracellular signal transduction via TLR4 (Toll-like receptor 4), which is a functional cell surface receptor, after binding with CD14 (see, for example, Non-patent document 3), whereby various cell responses represented by the production of inflammatory mediators are initiated. Therefore, it is considered that a substance capable of suppressing the intracellular signal transduction or cell activation induced by endotoxin, and various cell responses, which are induced by such intracellular signal transduction or cell activation and represented by the overproduction of inflammatory mediators such as TNF-α, can be effective prophylactic and therapeutic agents for sepsis (see, for example, Non-patent documents 3 and 4, and Patent documents 1 and 2).

Intracellular signal transduction or cell activation induced by endotoxin, and various cell responses such as the overproduction of inflammatory mediators including TNF-α, etc. induced by the intracellular signal transduction or cell activation lead to development and progress of various diseases such as ischemic brain disorder, arteriosclerosis, poor prognosis after coronary angioplasty, heart failure, diabetes, diabetic complications, arthritis, osteoporosis, osteopenia, autoimmune diseases, tissue disorders and rejection after organ transplantation, bacterial infection, viral infection, gastritis, pancreatitis, nephritis, pneumonia, hepatitis, and leukemia, in addition to the above-described sepsis (for example, Non-patent document 5 and Patent document 3).

The present inventors made intensive studies in order to solve the above problems, and as a result, they found that there are a group of compounds having a desired effect among substituted cycloalkene derivatives (Patent document 4). However, substituted cycloalkene derivatives (in the free form) are amorphous and have hygroscopicity. In view of this, the present inventors studied pharmacologically acceptable salts thereof. However, it was not easy to find crystals having storage and handling stability, and therefore industrialization thereof was extremely difficult.

PRIOR ART DOCUMENTS

Patent Documents

Patent Document 1: JP-A-2000-178246
Patent Document 2: JP-A-2004-2370
Patent Document 3: WO 2000/41698
Patent Document 4: WO 2007/032362

Non-Patent Documents

Non-patent Document 1: Iqbal et al., Expert Opin. Emerging Drugs, Vol. 7, page 111, 2002
Non-patent Document 2: Hawkins et al., Current Topics in Medicinal Chemistry, Vol. 4, page 1147, 2004
Non-patent Document 3: Beutler, Nature, Vol. 430, pages 257-263, 2004
Non-patent Document 4: Kakutani et al., Inflammation Research, Vol. 48, page 461, 1999
Non-patent Document 5: Donald N. Cook et al., Nature Immunology, Vol. 5, pages 975-979, 2004

SUMMARY OF THE INVENTION

Problems to be Solved by the Invention

An object of the present invention is to provide crystals of substituted cycloalkene derivatives having excellent storage and handling stability.

Means for Solving the Problems

That is, the present invention is directed to:

(1) potassium(2-chloro-4-fluorophenyl){[(2R,3R,8R)-7-(ethoxycarbonyl)-2,3-bis(hydroxymethyl)-1,4-dioxaspiro[4.5]deca-6-en-8-yl]sulfonyl}azanide represented by the following formula (1):

[Chemical Formula 1]

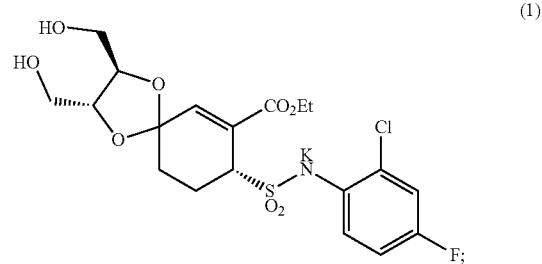

(2) potassium(2-bromo-4-fluorophenyl){[(2R,3R,8R)-7-(ethoxycarbonyl)-2,3-bis(hydroxymethyl)-1,4-dioxaspiro[4.5]deca-6-en-8-yl]sulfonyl}azanide represented by the following formula (2):

[Chemical Formula 2]

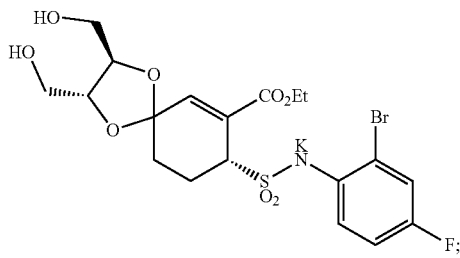

(2)

(3) a crystal of the compound according to the above (1);

(4) the crystal according to the above (3), which has the X-ray diffraction pattern shown in FIG. 1 in powder X-ray diffraction obtained by irradiation with copper Kα radiation;

(5) the crystal according to the above (3), which shows characteristic peaks at diffraction angles 2ζ (°) of 3.82, 7.64, 11.48, 19.06, 23.08, 25.22, and 26.98 (±2, respectively) in powder X-ray diffraction obtained by irradiation with copper Kα radiation;

(6) a crystal of the compound according to the above (2);

(7) the crystal according to the above (6), which has the X-ray diffraction pattern shown in FIG. 2 in powder X-ray diffraction obtained by irradiation with copper Kα radiation;

(8) the crystal according to the above (6), which shows characteristic peaks at diffraction angles 2θ (°) of 7.66, 15.36, 19.08, 23.76, 25.26, and 27.04 (±2, respectively) in powder X-ray diffraction obtained by irradiation with a copper Kα radiation;

(9) a pharmaceutical composition, comprising the compound according to the above (1) or (2) as an active ingredient;

(10) a pharmaceutical composition, comprising the compound according to the above (1) or (2) as an active ingredient, for use in suppressing the production of an inflammatory mediator caused by intracellular signal transduction or cell activation induced by endotoxin;

(11) a prophylactic and/or therapeutic agent for sepsis, comprising the compound according to the above (1) or (2) as an active ingredient;

(12) a pharmaceutical composition, comprising the crystal according to any one of the about (1) to (8);

(13) a method for producing the compound according to the above (1), characterized by adding a solution of potassium 2-ethylhexanoate hydrate in ethyl acetate dropwise to a solution or suspension of ethyl(2R,3R,8R)-8-[N-(2-chloro-4-fluorophenyl)sulfamoyl]-2,3-bis(hydroxymethyl)-1,4-dioxaspiro[4.5]deca-6-ene-7-carboxylate; or

(14) a method for producing the compound according to the above (2), characterized by adding ethyl(2R,3R,8R)-8-[N-(2-bromo-4-fluorophenyl)sulfamoyl]-2,3-bis(hydroxymethyl)-1,4-dioxaspiro[4.5]deca-6-ene-7-carboxylate dropwise to a solution of potassium 2-ethylhexanoate hydrate in ethyl acetate.

Advantage of the Invention

According to the present invention, crystals of substituted cycloalkene derivatives having excellent storage and handling stability can be provided. Potassium salts (crystals) of substituted cycloalkene derivatives according to the present invention suppress the production of an inflammatory mediator caused by intracellular signal transduction or cell activation induced by endotoxin and are effective as a prophylactic and/or therapeutic agent for sepsis.

MODE FOR CARRYING OUT THE INVENTION

Figure 1:
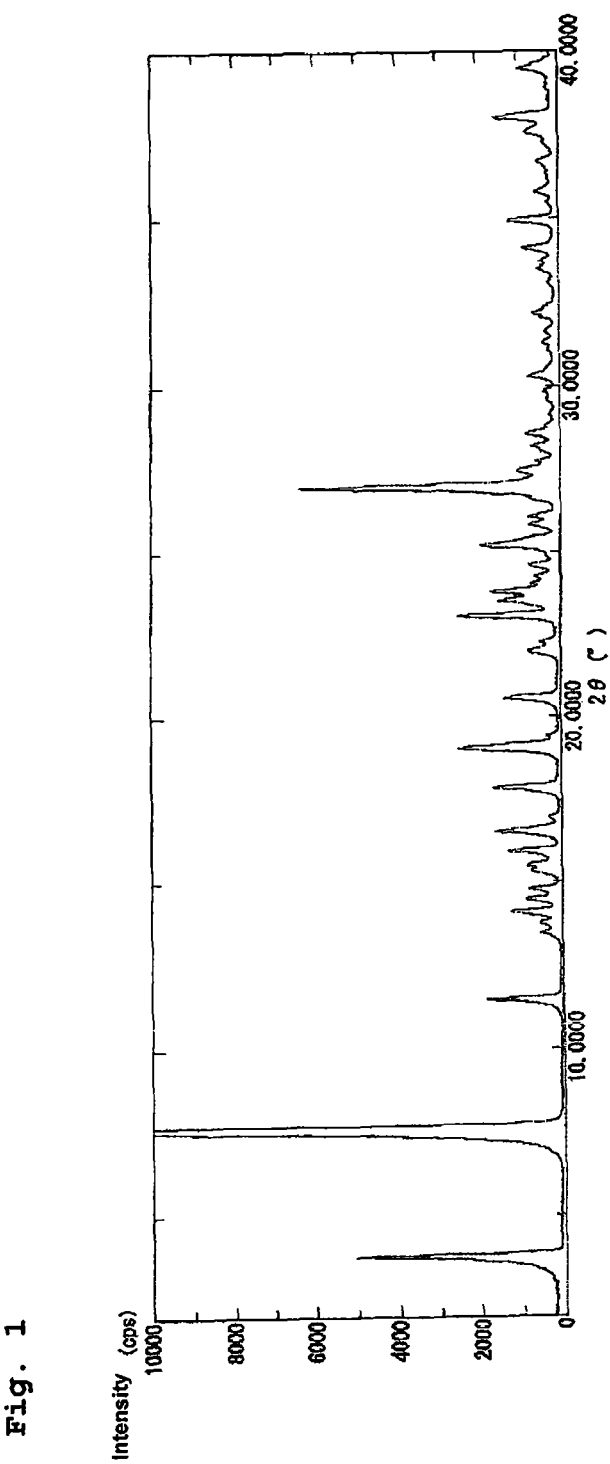
FIG. 1 shows a powder X-ray diffraction pattern of a crystal obtained in Example 1. In the drawing, the ordinate indicates diffraction intensity in units of counts/sec (cps), and the abscissa indicates the value of diffraction angle 2θ.

The present invention relates to a crystal of potassium(2-chloro-4-fluorophenyl){[(2R,3R,8R)-7-(ethoxycarbonyl)-2,3-bis(hydroxymethyl)-1,4-dioxaspiro[4.5]deca-6-en-8-yl]sulfonyl}azanide represented by the following formula (1) (hereinafter sometimes referred to as Compound (1) in this description):

[Chemical Formula 3]

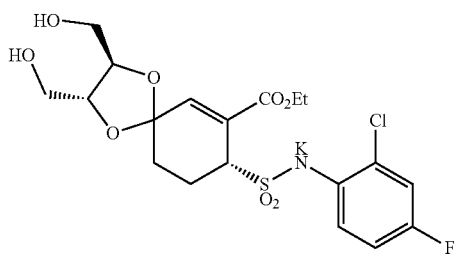

(1)

or potassium(2-bromo-4-fluorophenyl){[(2R,3R,8R)-7-(ethoxycarbonyl)-2,3-bis(hydroxymethyl)-1,4-dioxaspiro[4.5]deca-6-en-8-yl]sulfonyl}azanide represented by the following formula (2) (hereinafter sometimes referred to as Compound (2) in this description).

[Chemical Formula 4]

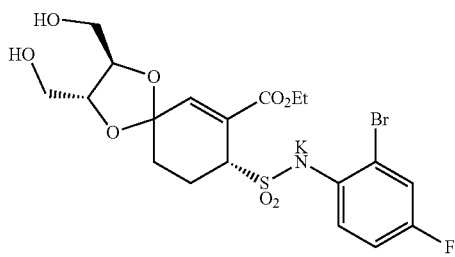

(2)

Here, a crystal refers to a solid whose internal structure is three-dimensionally composed of a regular repetition of constituent atoms (or a group thereof), and is distinguished from an amorphous solid which does not have such a regular internal structure. Whether or not a solid is a crystal can be examined by a known crystallographic method (such as powder X-ray diffraction measurement or differential scanning calorimetric analysis). For example, a solid is subjected to powder X-ray diffraction measurement using an X-ray obtained by irradiation with copper Kα radiation. The solid is determined to be a crystal when distinct peaks are observed in the X-ray diffraction pattern, while the solid is determined to be amorphous when no distinct peaks are observed. The solid is determined to be a crystal whose crystallinity is low when the peaks can be read but are not distinct (for example, broad), and such a crystal whose crystallinity is low is also encompassed within the crystal of the present invention.

Even the same compound can form crystals having a plurality of different internal structures and physicochemical properties (crystal polymorphism) depending on the conditions for crystallization. The crystal of the present invention may be any of these crystal polymorphic forms and may be a mixture of two or more crystal polymorphic forms.

The crystal of the present invention may sometimes form a hydrate by allowing the crystal to stand in the air to absorb water, thereby having attached water, or by heating the crystal to 25 to 150° C. in usual atmospheric conditions, etc. Further, the crystal of the present invention may sometimes contain a solvent used at the time of crystallization as an attached residual solvent or a solvate.

In this description, the crystal of the present invention is sometimes represented on the basis of powder X-ray diffraction data. In powder X-ray diffraction, the measurement and analysis may be performed by methods conventionally used in this field, and for example, the powder X-ray diffraction can be performed by the method described in the Examples. Further, in general, in the case of a hydrated or dehydrated crystal, the lattice constant thereof is changed by the addition or removal of water of crystallization, and therefore the diffraction angle (2θ) in powder X-ray diffraction may sometimes be changed. Further, the peak intensity may sometimes be changed due to a difference in a crystal growth surface or the like (crystal habit), etc. Therefore, when the crystal of the present invention is represented on the basis of powder X-ray diffraction data, a crystal having an identical peak diffraction angle and X-ray diffraction pattern in powder X-ray diffraction, and also hydrated and dehydrated crystals obtained from the crystal, are encompassed within the scope of the present invention.

In powder diffraction measurement using copper Kα radiation, generally, a sample is irradiated with copper Kα radiation (in which Kα1 and Kα2 radiations are not separated). An X-ray diffraction pattern can be obtained by analyzing diffraction derived from Kα radiation, and can also be obtained by analyzing only diffraction derived from Kα1 radiation taken from diffraction derived from Kα radiation. In the present invention, the powder X-ray diffraction pattern obtained by irradiation with Kα radiation includes an X-ray diffraction pattern obtained by analyzing diffraction peaks derived from Kα radiation and an X-ray diffraction pattern obtained by analyzing diffraction derived from Kα1 radiation, and is preferably an X-ray diffraction pattern obtained by analyzing diffraction derived from Kα1 radiation.

One preferred embodiment of the crystal of the present invention is a crystal of potassium(2-chloro-4-fluorophenyl){[(2R,3R,8R)-7-(ethoxycarbonyl)-2,3-bis(hydroxymethyl)-1,4-dioxaspiro[4.5]deca-6-en-8-yl]sulfonyl}azanide referred to as Compound (1). The crystal of Compound (1) has the X-ray diffraction pattern shown in FIG. 1 in a powder diffraction pattern obtained by irradiation with copper Kα radiation. Further, the crystal of Compound (1) has characteristic peaks at diffraction angles 2θ (°) of 3.82, 7.64, 11.48, 19.06, 23.08, 25.22, and 26.98. Here, the "characteristic peak" refers to a peak having a relative intensity of 9 or more when the maximum peak intensity in the powder X-ray diffraction is taken as 100.

Another preferred embodiment of the crystal of the present invention is a crystal of potassium(2-bromo-4-fluorophenyl){[(2R,3R,8R)-7-(ethoxycarbonyl)-2,3-bis(hydroxymethyl)-1,4-dioxaspiro[4.5]deca-6-en-8-yl]sulfonyl}azanide referred to as a crystal of Compound (2). The crystal of Compound (2) has the X-ray diffraction pattern shown in FIG. 2 in a powder diffraction pattern obtained by irradiation with copper Kα radiation. Further, the crystal of Compound (2) has characteristic peaks at diffraction angles 2θ (°) of 7.66, 15.36, 19.08, 23.76, 25.26, and 27.04. Here, the "characteristic peak" refers to a peak having a relative intensity of 10 or more when the maximum peak intensity in the powder X-ray diffraction is taken as 100.

Figure 2:
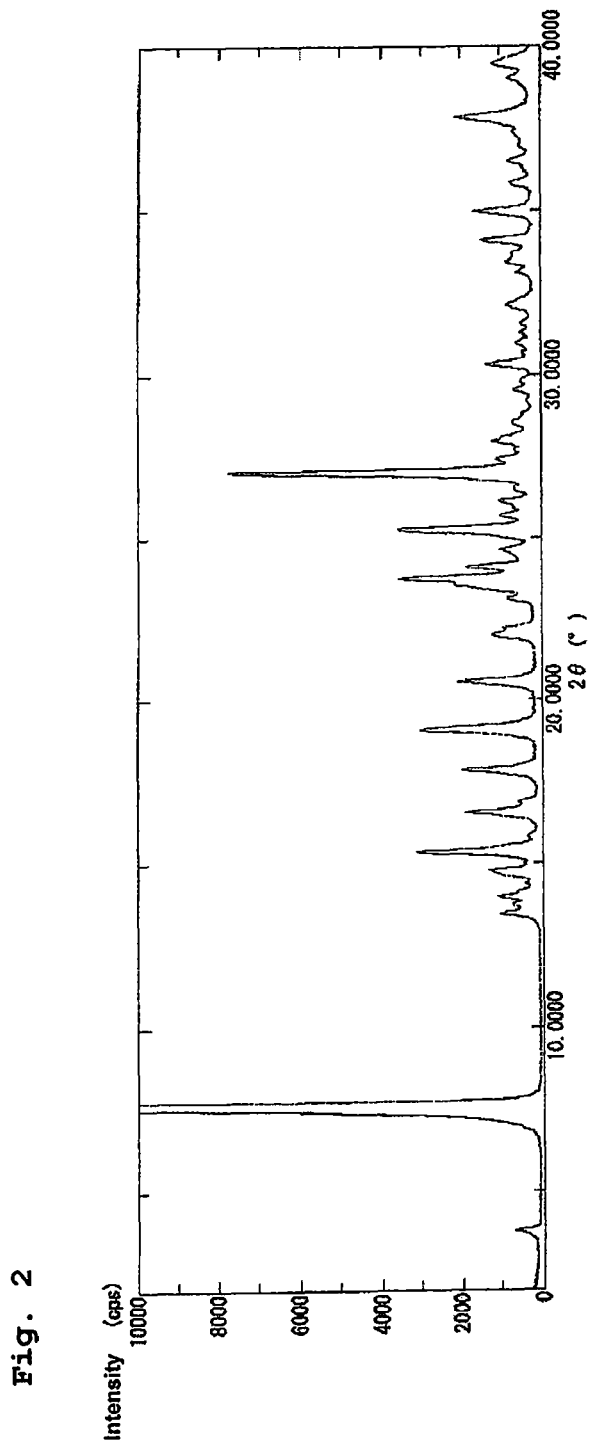
FIG. 2 shows a powder X-ray diffraction pattern of a crystal obtained in Example 2. In the drawing, the ordinate indicates diffraction intensity in units of counts/sec (cps), and the abscissa indicates the value of diffraction angle 2θ.

In the powder X-ray diffraction patterns shown in FIGS. 1 and 2, the ordinate indicates diffraction intensity [counts/sec (cps)], and the abscissa indicates the diffraction angle 2θ (°). The 2θ can be slightly changed in its position and relative intensity depending on the measurement conditions and the like, therefore even when 2θ is slightly changed, the identification of the crystal form should be appropriately determined by reference to the pattern of the entire spectrum. The limit of such error is generally within the range of ±2, preferably within the range of ±1, more preferably within the range of ±0.5, further more preferably within the range of ±0.2.

Further, as is well known in the field of crystallography, also the intensities of the respective diffraction peaks can be changed by various factors (including preferred orientation occurring in a specific crystalline form and the effect of grain size), and therefore, the relative intensities of the above-described main peaks for identifying the crystal of the present invention can also be changed, and these crystals are also encompassed within the crystal of the present invention.

The Compound (1) or (2) of the present invention has activity to suppress the production of an inflammatory mediator caused by intracellular signal transduction or cell activation induced by endotoxin, and also has excellent storage and handling stability, and therefore is useful as a pharmaceutical. Further such a pharmaceutical is preferably used for warm-blooded animals, more preferably used for humans.

In the case where Compound (1) and Compound (2) of the present invention are used as a therapeutic agent or a prophylactic agent for the above-described diseases, the compound per se or as a mixture with an appropriate pharmacologically acceptable excipient, diluent, or the like can be administered orally in the form of a tablet, a capsule, a granule, a powder, a syrup, or the like, or parenterally in the form of an injection, a suppository, or the like.

These pharmaceutical preparations are prepared in accordance with known methods using additives such as an excipient (for example, an organic excipient such as a sugar derivative such as lactose, sucrose, glucose, mannitol, or sorbitol; a starch derivative such as corn starch, potato starch, pregelatinized starch or dextrin; a cellulose derivative such as crystalline cellulose; gum arabic; dextrane; or pullulan; or an inorganic excipient such as a silicate derivative such as light silicic anhydride, synthetic aluminum silicate, calcium silicate, or magnesium aluminometasilicate; a phosphate such as calcium hydrogen phosphate; a carbonate such as calcium carbonate; or a sulfate such as calcium sulfate can be used), a lubricant (for example, stearic acid, a metal salt of stearic acid such as calcium stearate or magnesium stearate; talc; a wax such as beeswax or spermaceti wax; boric acid; adipic acid; a sulfate such as sodium sulfate; glycol; fumaric acid; sodium benzoate; D- or L-leucine; a lauryl sulfate such as sodium lauryl sulfate or magnesium lauryl sulfate; a silicic acid such as silicic anhydride or silicate hydrate; or any of the above-described starch derivatives can be used), a binder (for example, hydroxypropyl cellulose, hydroxypropyl methyl cellulose, polyvinylpyrrolidone, macrogol, or a compound similar to any of the above-described excipients can be used), a disintegrant (for example, a cellulose derivative such as low-substituted hydroxypropyl cellulose, carboxymethyl cellulose, calcium carboxymethyl cellulose, or internally crosslinked sodium carboxymethyl cellulose; a chemically modified water-soluble polymer such as carboxymethyl starch, sodium carboxymethyl starch, or crosslinked polyvinylpyrrolidone; or any of the above-described starch derivatives can be used), an emulsifier (for example, a colloidal clay such as bentonite or veegum; a metal hydroxide such as magnesium hydroxide or aluminum hydroxide; an anionic surfactant such as sodium lauryl sulfate or calcium stearate; a cationic surfactant such as benzalkonium chloride; or a nonionic surfactant such as a polyoxyethylene alkyl ether, a polyoxyethylene sorbitan fatty acid ester, or a sucrose fatty acid ester can be used), a stabilizer (for example, a paraoxybenzoic acid ester such as methyl paraben or propyl paraben; an alcohol such as chlorobutanol, benzyl alcohol, or phenylethyl alcohol; benzalkonium chloride; a phenol such as phenol or cresol; thimerosal; dehydroacetic acid; or sorbic acid can be used) and a corrigent (for example, a commonly used sweetener, acidifier, flavor, or the like can be used) or a diluent.

EXAMPLES

Hereinafter, the present invention will be described in further detail with reference to Examples and Test Examples.

Example 1

Potassium(2-chloro-4-fluorophenyl){[(2R,3R,8R)-7-(ethoxycarbonyl)-2,3-bis(hydroxymethyl)-1,4-dioxaspiro[4.5]deca-6-en-8-yl]sulfonyl}azanide

[Chemical Formula 5]

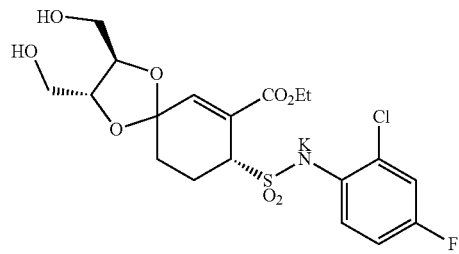

100 mg (0.208 mmol) of ethyl (2R,3R,8R)-8-[N-(2-chloro-4-fluorophenyl)sulfamoyl]-2,3-bis(hydroxymethyl)-1,4-dioxaspiro[4.5]deca-6-ene-7-carboxylate [a compound described as a low polarity compound (first peak) of Example 162 in WO 2007/032362] was dissolved in 1 mL of ethyl acetate, and 2 mL of a solution containing 38 mg (0.208 mmol) of potassium 2-ethylhexanoate hydrate in ethyl acetate was added thereto under stirring at room temperature. The resulting reaction solution was concentrated under reduced pressure, and to the residue, diethyl ether was added. A precipitated solid was obtained by filtration and washed with diethyl ether, whereby 92 mg of a crude product was obtained as an amorphous solid. Then, the crude product was dissolved in ethyl acetate, and the resulting solution was heated under reflux at 130° C. for 2 hours. After the resulting mixture was cooled, a precipitated solid was obtained by filtration and washed with ethyl acetate, whereby the title compound was obtained as a white crystal.

$^1$H-NMR spectrum (400 MHz, DMSO-$d_6$) δ ppm:
7.40 (1H, dd, J=9 Hz, 6 Hz), 7.07-6.97 (1H, m), 6.84-6.75 (1H, m), 6.46 (1H, s),
4.98 (1H, t, J=6 Hz), 4.82 (1H, t, J=6 Hz), 4.11-4.02 (1H, m), 4.02-3.93 (1H, m),
3.93-3.80 (3H, m), 3.63-3.41 (4H, m), 2.78-2.65 (1H, m), 2.34-2.25 (1H, m),
1.87-1.74 (1H, m), 1.65-1.58 (1H, m), 1.14 (3H, t, J=7 Hz)

The powder X-ray diffraction pattern is shown in FIG. 1.
<Another Method>

300 mg (0.625 mmol) of ethyl(2R,3R,8R)-8-[N-(2-chloro-4-fluorophenyl)sulfamoyl]-2,3-bis(hydroxymethyl)-1,4-dioxaspiro[4.5]deca-6-ene-7-carboxylate was dissolved in 2 mL of ethyl acetate, and 4 mL of a solution containing 114 mg (0.625 mmol) of potassium 2-ethylhexanoate hydrate in ethyl acetate was added thereto under stirring at room temperature. The resulting reaction solution was concentrated under reduced pressure, and to the residue, diethyl ether was added. A precipitated solid was obtained by filtration and washed with diethyl ether, whereby a crude product was obtained as an amorphous solid. Then, the crude product was dissolved in 3 mL of ethyl acetate, and a seed crystal obtained by the above-described method was added thereto, and the resulting mixture was heated under reflux at 100° C. for 5 minutes. After the resulting mixture was cooled, a precipitated solid was obtained by filtration and washed with ethyl acetate, whereby 236 mg of the title compound was obtained as a white crystal (yield: 73%).

Example 2

Potassium(2-bromo-4-fluorophenyl){[(2R,3R,8R)-7-(ethoxycarbonyl)-2,3-bis(hydroxymethyl)-1,4-dioxaspiro[4.5]deca-6-en-8-yl]sulfonyl}azanide

[Chemical Formula 6]

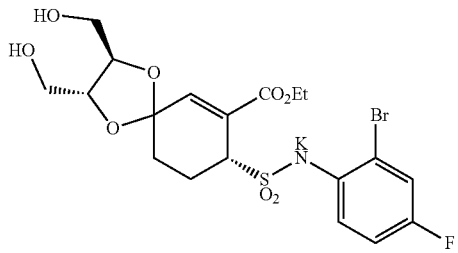

422 mg (2.31 mmol) of potassium 2-ethylhexanoate hydrate was dissolved in 23 mL of ethyl acetate, and 1.215 g (2.31 mmol) of ethyl(2R,3R,8R)-8-[N-(2-bromo-4-fluorophenyl)sulfamoyl]-2,3-bis(hydroxymethyl)-1,4-dioxaspiro[4.5]deca-6-ene-7-carboxylate [a compound described as a low polarity compound (first peak) of Example 166 in WO 2007/032362] was added thereto under stirring at room temperature. The resulting reaction solution was concentrated under reduced pressure, and to the residue, diethyl ether was added. A precipitated solid was obtained by filtration and washed with diethyl ether, whereby 954 mg of a crude product was obtained as an amorphous solid. Then, the crude product was dissolved in 6 mL of ethyl acetate, and the resulting solution was heated under stirring at 70° C. for 5 minutes. After the resulting mixture was cooled, a precipitated solid was obtained by filtration and washed with ethyl acetate and diethyl ether, whereby 850 mg of the title compound was obtained as a white crystal (yield: 65%).

$^1$H-NMR spectrum (400 MHz, DMSO-$d_6$) δ ppm:
7.39 (1H, dd, J=9 Hz, 6 Hz), 7.17 (1H, dd, J=9 Hz, 3 Hz), 6.83 (1H, dt, J=9 Hz, 3 Hz), 6.45 (1H, s), 4.98 (1H, t, J=5 Hz), 4.83 (1H, t, J=5 Hz), 4.13-3.81 (5H, m), 3.64-3.41 (4H, m), 2.84-2.63 (1H, m), 2.35-2.26 (1H, m), 1.85-1.73 (1H, m), 1.65-1.56 (1H, m), 1.14 (3H, t, J=7 Hz)

The powder X-ray diffraction pattern is shown in FIG. 2.
<Another Method>
102 mg (0.560 mmol) of potassium 2-ethylhexanoate hydrate was dissolved in 5 mL of ethyl acetate, and 280 mg (0.534 mmol) of ethyl (2R,3R,8R)-8-[N-(2-bromo-4-fluorophenyl)sulfamoyl]-2,3-bis(hydroxymethyl)-1,4-dioxaspiro[4.5]deca-6-ene-7-carboxylate was added thereto under stirring at room temperature. The resulting reaction solution was concentrated under reduced pressure, and to the residue, diethyl ether was added. A precipitated solid was obtained by filtration and washed with diethyl ether, whereby a crude product was obtained as an amorphous solid. Then, the crude product was dissolved in 1 mL of ethanol, and the resulting solution was heated under stirring at 70° C. for 1 minute. After the resulting mixture was cooled, a precipitated solid was obtained by filtration and washed with ethanol and diethyl ether, whereby 197 mg of the title compound was obtained as a white crystal (yield: 66%).

Example 3

Measurement of Powder X-Ray Diffraction

Rint TTR-III (provided with a scintillation counter tube and a long slit for removing $K_\beta$ radiations) manufactured by Rigaku Corporation was used. A sample was placed uniformly on a non-reflective sample holder, and measurement was performed under the following conditions.
<Analytical Conditions>
X-ray species: Cu-Kα (wavelength: 1.54 A), Tube voltage: 50 kV, Tube current: 300 mA, Scanning rate: 2°/min, Step: 0.02°, Scanning range (2q): 2° to 60°, Divergence slit: 0.5 mm, Scattering slit: 0.5 mm, Receiving slit: 0.5 mm
<Measurement Results>
The powder X-ray diffraction pattern obtained by measuring the crystal of the compound obtained in Example 1 in accordance with the above-described method is shown in FIG. 1. Peaks having a relative intensity of 9 or more when the maximum peak intensity in FIG. 1 is taken as 100 are shown in Table 1.

TABLE 1

| 2θ | d value | Relative intensity |
|---|---|---|
| 3.82 | 23.11 | 24 |
| 7.64 | 11.56 | 100 |
| 11.48 | 7.70 | 9 |
| 19.06 | 4.65 | 12 |
| 23.08 | 3.85 | 12 |
| 25.22 | 3.53 | 9 |
| 26.98 | 3.30 | 30 |

The powder X-ray diffraction pattern obtained by measuring the crystal of the compound obtained in Example 2 in accordance with the above-described method is shown in FIG. 2. Peaks having a relative intensity of 10 or more when the maximum peak intensity in FIG. 2 is taken as 100 are shown in Table 2.

TABLE 2

| 2θ | d value | Relative intensity |
|---|---|---|
| 7.66 | 11.53 | 100 |
| 15.36 | 5.76 | 12 |
| 19.08 | 4.65 | 11 |
| 23.76 | 3.74 | 13 |
| 25.26 | 3.52 | 13 |
| 27.04 | 3.29 | 28 |

Example 4

Moisture Absorption Test

A sample was weighed in a glass sample cup, and the weight thereof was measured under the following conditions.
<Measurement Conditions>
Measuring device: DVS Advantage, manufactured by Surface Measurement System Ltd.
Measurement humidity: 10, 20, 30, 40, 50, 60, 65, 70, 75, 80, 85, 90, 95, 95, 90, 85, 80, 75, 70, 65, 60, 50, 40, 30, 25, 20, and 10% RH Measurement temperature: 25° C., Minimum exposure time: 15 min, Maximum exposure time: 120 min, Step transition condition: within 0.006 wt. %

The appearance of the sample at the time of completion of the measurement was confirmed.

<Measurement Results>

Figure 3:
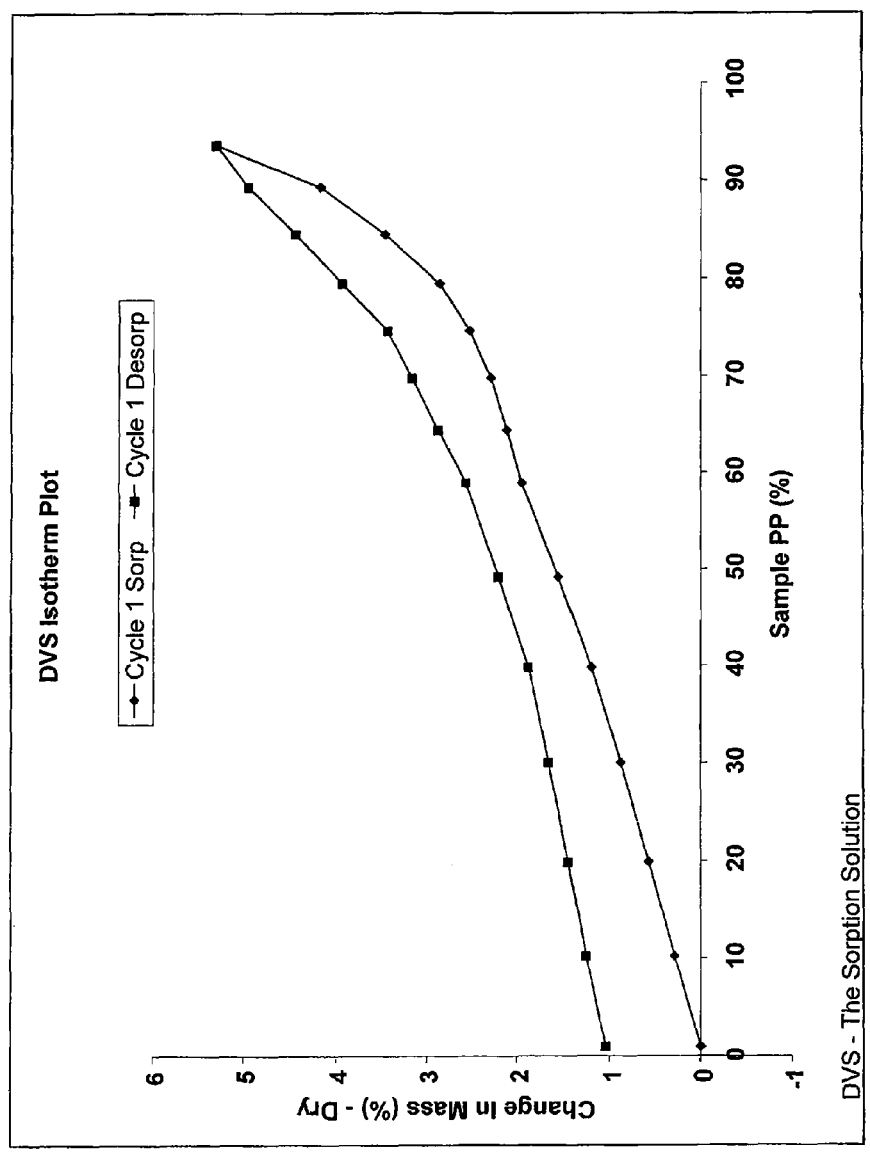
FIG. 3 shows moisture absorption and desorption equilibrium curves of a compound (in the free form) of Comparative Example in a moisture absorption test. In the drawing, the ordinate indicates the weight of a sample, and the abscissa indicates the measurement humidity. "Cycle 1 Sorp" represents "a moisture absorption equilibrium curve (in the first cycle)", and change in weight against relative humidity at the time of obtaining a constant weight when the humidity was increased is plotted. "Cycle 1 Desorp" represents "a moisture desorption equilibrium curve (in the first cycle)", and change in weight against relative humidity at the time of obtaining a constant weight when the humidity was decreased is plotted.
Figure 4:
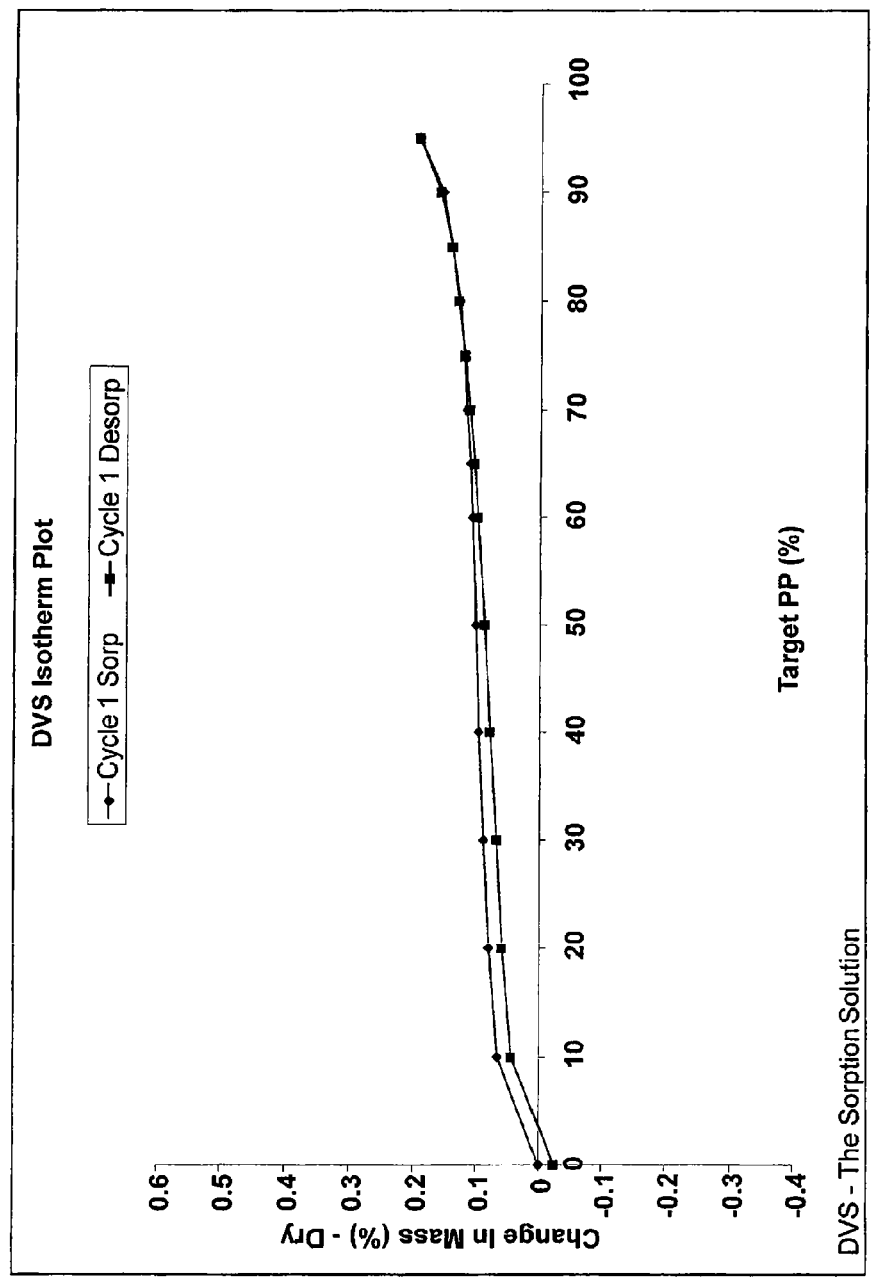
FIG. 4 shows moisture absorption and desorption equilibrium curves of a compound of Example 1 in a moisture absorpotion test. In the drawing, the ordinate indicates the change in weight of a sample, and the abscissa indicates the set measurement humidity. "Cycle 1 Sorp" represents "a moisture absorption equilibrium curve (in the first cycle)", and change in weight against relative humidity at the time of obtaining a constant weight when the humidity was increased is plotted. "Cycle 1 Desorp" represents "a moisture desorption equilibrium curve (in the first cycle)", and change in weight against relative humidity at the time of obtaining a constant weight when the humidity was decreased is plotted.
Figure 5:
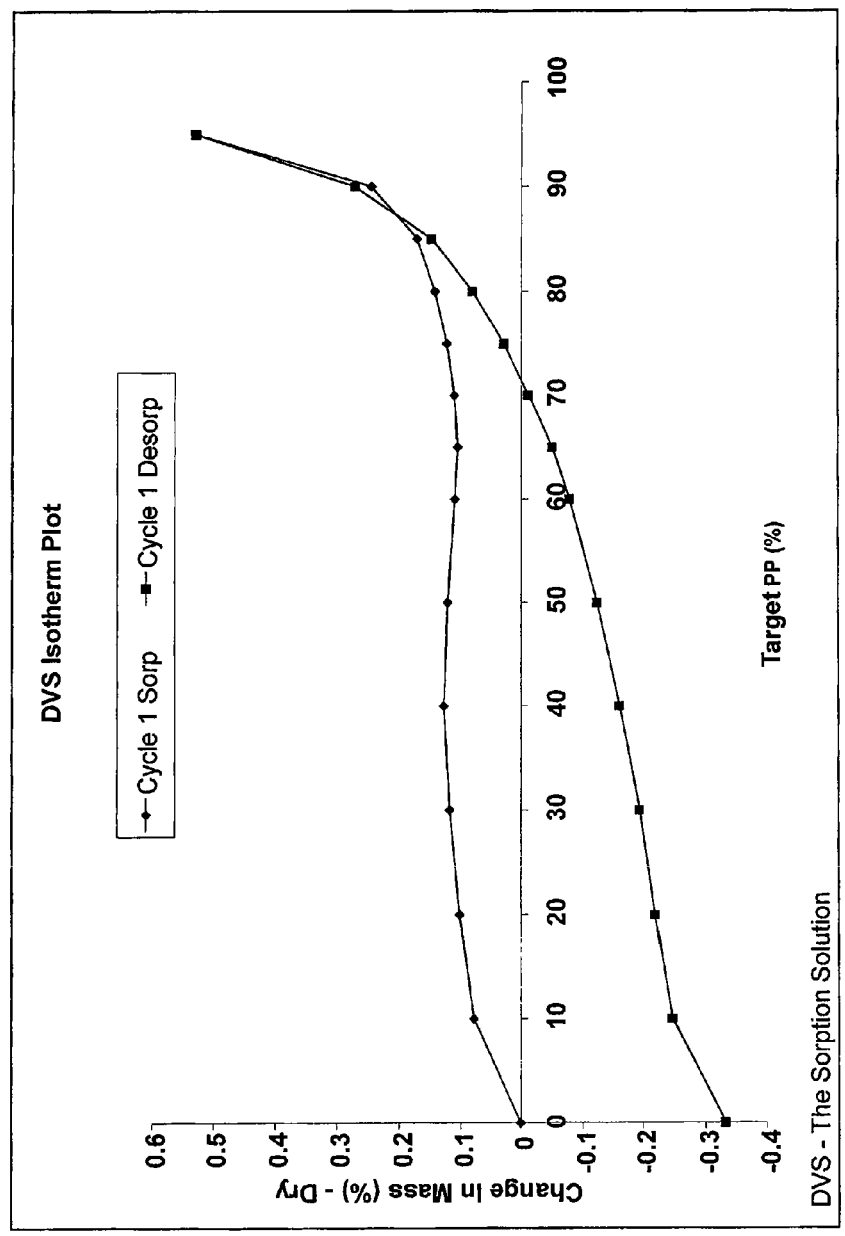
FIG. 5 shows moisture absorption and desorption equilibrium curves of a compound of Example 2 in a moisture absorption test. In the drawing, the ordinate indicates the change in weight of a sample, and the abscissa indicates the set measurement humidity. "Cycle 1 Sorp" represents "a moisture absorption equilibrium curve (in the first cycle)", and change in weight against relative humidity at the time of obtaining a constant weight when the humidity was increased is plotted. "Cycle 1 Desorp" represents "a moisture desorption equilibrium curve (in the first cycle)", and change in weight against relative humidity at the time of obtaining a constant weight when the humidity was decreased is plotted.

As shown in Table 4 and FIGS. 3, 4, and 5, ethyl(2R,3R,8R)-8-[N-(2-chloro-4-fluorophenyl)sulfamoyl]-2,3-bis(hydroxymethyl)-1,4-dioxaspiro[4.5]deca-6-ene-7-carboxylate (a compound in the free form described as a low polarity compound (first peak) of Example 162 in WO 2007/02362) used as the compound of Comparative Example showed high hygroscopicity at every measurement humidity (see FIG. 3), however, the compounds of Examples 1 and 2 did not show hygroscopicity (see FIGS. 4 and 5). In particular, the compound of Example 1 did not show hygroscopicity at any measurement humidity in a consistent manner (see FIG. 4).

Example 5

Solubility Test

<Test Method>

150 mg of each of the compounds of Examples 1 and 2 and Comparative Example 1 was dissolved in 5 mL of an aqueous phosphate solution containing sodium chloride (containing 150 mM NaCl and 10 mM $NaH_2PO_3.2H_2O$). After the resulting mixture was stirred for 30 minutes while measuring the pH of the mixture, a 0.5 mL portion of the resulting suspension was taken and filtered through a syringe filter. A 100 μL portion of the obtained filtrate was transferred into a 10-mL volumetric flask and diluted to 10 mL with an aqueous solution of 50% MeCN, whereby a sample solution was prepared. To the suspension, concentrated HCl was added dropwise to adjust the pH thereof to around 7.5.

Measurement was performed using HPLC under the following conditions.

<Analytical Method Conditions>

HPLC system: Water's Alliance
Column: XTerra MS C18 3.5 μm, Column Size: 4.6×100 mm
Column Temp: 40° C., Flow Rate: 1.2 mL/min
Solvent A: 0.1% phosphoric acid in water, Solvent B: 0.1% phosphoric acid in MeCN
Gradient Schedule

TABLE 3

| Time | Total flow | % A | % B | Curve |
|---|---|---|---|---|
| 0 | 1.2 | 95 | 5 | |
| 15 | 1.2 | 5 | 95 | 6 |
| 15.01 | 1.2 | 95 | 5 | 11 |
| 20 | 1.2 | 95 | 5 | 6 |

<Measurement Results>

As shown in Table 4, the compound (in the free form) of Comparative Example had low solubility. Meanwhile, the compounds of Examples 1 and 2 showed a solubility of 13.8 mg/mL and 9.6 mg/mL, respectively.

Example 6

Solution Stability Test

<Test Method>

Each of the compounds (Examples 1 and 2 and Comparative Example) of the present invention was precisely weighed and placed in a 10-mL volumetric flask and dissolved in PBS at pH 6. Then, 1 N HCl was added thereto to adjust the solution of the compound of Example 1 to pH 6, the solution of the compound of Example 2 to pH 7, and the solution of the compound of Comparative Example to pH 8. The above flasks as such and the flasks covered with aluminum foil for light shielding as controls were placed in a light tester at 25° C. After one day, each solution was diluted to 10 mL with 50% MeCN. The concentration of each solution was calculated by performing HPLC under the same conditions as used in the above-described solubility test, and the change in concentration from the control was calculated.

<Measurement Results>

As shown in Table 4, the values for the solution stability after storage for 1 day were 99.4% in the case of the compound (in the free form) of Comparative Example, 99.9% in the case of the compound of Example 1, and 99.4% in the case of the compound of Example 2.

Example 7

Evaluation for Chemical Stability

<Test Method>

In a low-humidity room (25° C., 30% RH), a sample was precisely weighed in a quartz sample cup and placed in a 10-mL volumetric flask. Then, the flask was left in a desiccator containing silica gel for 3 days while keeping the mouth of the flask open. Thereafter, the flask was further stored in an environment at a temperature of 25° C. and a humidity of 30% for 4 weeks while keeping the mouth of the flask open. Then, the residual amount was measured by performing HPLC under the same conditions as used in the solubility test in Example 5.

<Measurement Results>

As shown in Table 4, it was impossible to perform this test for the compound (in the free form) of Comparative Example because the compound is hygroscopic, however, the compounds of Examples 1 and 2 showed a residual amount of 98.9% and 98.8%, respectively, which revealed that the compounds of Examples 1 and 2 are stable.

TABLE 4

| | Comparative Example | Example 1 | Example 2 |
|---|---|---|---|
| Free form or potassium salt | Free form | Potassium salt | Potassium salt |
| Crystalline form | Amorphous | Crystalline | Crystalline |
| Hygroscopicity | With hygroscopicity 2.6% (relative humidity 10→80%) Changed into candy-like form | Without hygroscopicity <0.1% (relative humidity 10→80%) no change in appearance | Without hygroscopicity <0.1% (relative humidity 10→80%) no change in appearance |
| Solubility (PBS pH 7.5) | Since the compound is transformed into a viscous solid in an aqueous solution, it was impossible to measure the concentration in a reproducible manner. | 13.8 mg/ml | 9.6 mg/ml |

TABLE 4-continued

| | Comparative Example | Example 1 | Example 2 |
|---|---|---|---|
| Solution stability (25° C., 1 day) | 99.4% McIlvaine buffer pH 8 | 99.9% PBS pH 6 | 99.4% PBS pH 7 |
| Chemical stability (25° C., 4 weeks) | Due to high hygroscopicity, it was impossible to perform this test. | 98.9% (relative humidity 30%) | 98.8% (relative humidity 30%) |

Test Example 1

Suppressive Effect on Production of TNF-α in Cells Stimulated with Endotoxin (In Vitro)

The rate of suppression of TNF-α production when human monocytic cell line U937 was stimulated with endotoxin was determined for the compound of the present invention. Specifically, to RPMI-1640 medium containing 10% (volume %) of inactivated newborn bovine serum, 12-O-tetradecanoylphorbol-13-acetate was added to give a final concentration of 30 ng/ml. U937 cells were suspended in the medium and plated into a 96-well culture plate (Sumilon) so that the number of cells per well/volume was $2 \times 10^4/0.1$ mL, and the culture plate was then incubated for 3 days at 37° C. in a carbon dioxide incubator with 5% $CO_2$ and 100% humidity. After completion of the incubation, the culture supernatant was removed. The compound of the present invention was added to each well at different concentrations, and also lipopolysaccharide (LPS) (*E. coli* 0111:B4, Sigma) was added thereto to give a final concentration of 30 ng/ml. After the culture plate was incubated in the carbon dioxide incubator again for 4.5 hours, the culture supernatant was collected. By using a 384-well half area black plate (Greiner) and an HTRF quantitative determination kit manufactured by Cisbio International, the concentration of TNF-α in the culture supernatant was measured as time-resolved fluorescence by Discovery (Packard). From the measured value in the absence of LPS (X), the measured value in the absence of the compound of the present invention (Y), and the measured value in the presence of the compound of the present invention (Z), the rate of suppression of TNF-α production was obtained according to the following calculation formula [I].

Rate of suppression of TNF-α production (%)={1−(Z−X)/(Y−X)}×100 [I]

<Suppressive Effect on Production of TNF-α (In Vitro)>

TABLE 5

<Suppressive Effect on Production of TNF-α (in vitro)>

| Test compound | Rate of suppression of TNF-α production [%] (concentration of test compound: 100 nM) |
|---|---|
| Compound of Example 1 | 89 |

As shown in Table 5, in this test, the compound of the present invention showed an excellent suppressive effect on the production of TNF-α in cells stimulated with endotoxin.

Test Example 2

Suppressive Effect on Elevation of Blood TNF-α Level (In Vivo)

The suppressive effect of the compound of the present invention on the elevation of blood TNF-α level was studied. A test for the elevation of blood TNF-α level was performed in accordance with the method of Parant et al. described in Journal of Leukocyte Biology, Vol. 47, page 164 (1990).

In the test, 3 to 4 male Sprague Dawley rats (8 to 9 weeks of age) were used for each group.

At 4 hours before the administration of LPS, muramyl dipeptide dissolved in physiological saline (1 mg/mL) was administered to each rat through the tail vein at a dose of 1 mL/kg. At 0.5 hours before the administration of LPS, the rats were anaesthetized with pentobarbital (40 mg/kg), and the compound of the present invention dissolved in a 5% dimethyl acetamide/95% polyethylene glycol 400 solution was administered to each rat through the right femoral vein at a dose of 1 mL/kg. To the control group, a 5% dimethyl acetamide/95% polyethylene glycol 400 solution was administered at a dose of 1 mL/kg. LPS dissolved in physiological saline (3 µg/mL) was administered to each rat through the left femoral vein at a dose of 1 mL/kg. At 2 hours after the administration of LPS, the blood was collected using a 3.8% (w/v) sodium citrate solution as an anticoagulant, and the blood plasma was separated by centrifugation (10,000 g, 5 minutes, 4° C.). The plasma TNF-α level was determined using a TNF-α quantitative determination kit (BioSource International, Inc.). From the blood TNF-α level in the control group (X) and the blood TNF-α level in the group administered with the compound of the present invention (Y), the rate of suppression of TNF-α production was calculated according to the following calculation formula [II].

Rate of suppression of TNF-α production (%)={1−Y/X}×100 [II]

<Suppressive Effect on Production of TNF-α (In Vivo)>

TABLE 6

<Suppressive Effect on Production of TNF-α (in vivo)>

| Test compound | Rate of suppression of TNF-α production [%] (concentration of test compound: 0.3 mg/kg) |
|---|---|
| Compound of Example 1 | 96 |
| Compound of Example 2 | 81 |

As shown in Table 6, in this test, the compounds of the present invention showed an excellent suppressive effect on the elevation of blood TNF-α level.

INDUSTRIAL APPLICABILITY

According to the present invention, crystals of substituted cycloalkene derivatives having excellent storage and handling stability can be provided. The potassium salts of substituted cycloalkene derivatives of the present invention suppress the production of an inflammatory mediator caused by intracellular signal transduction or cell activation induced by endotoxin, and therefore are effective as a prophylactic and/or therapeutic agent for sepsis.

The invention claimed is:

1. A crystal of potassium (2-chloro-4-fluorophenyl){[(2R,3R,8R)-7-(ethoxycarbonyl)-2,3-bis(hydroxymethyl)-1,4-dioxaspiro[4.5]deca-6-en-8-yl]sulfonyl}azanide, represented by the following formula (1):

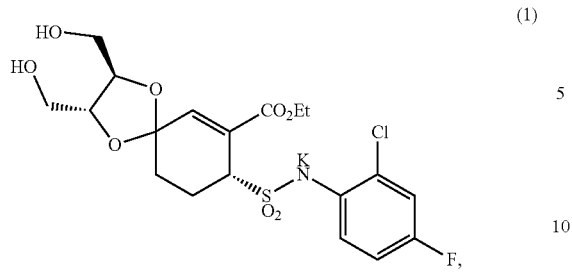
(1)

wherein the crystal shows characteristic peaks at diffraction angles 2θ of 3.82±2°, 7.64±2°, 11.48±2°, 19.06±2°, 23.08±2°, 25.22±2°, and 26.98±2° in powder X-ray diffraction obtained by irradiation with copper Kα radiation.

2. A pharmaceutical composition, comprising the crystal of claim 1 and one or more pharmaceutical additives.

3. A method for producing the crystal of claim 1, comprising adding a solution of potassium 2-ethylhexanoate hydrate in ethyl acetate dropwise to a solution or suspension of ethyl (2R,3R,8R)-8[N-(2-chloro-4-fluorophenyl)sulfamoyl]-2,3-bis(hydroxymethyl)-1,4-dioxaspiro[4.5]deca-6-ene-7-carboxylate.

4. A method of treating sepsis, comprising administering the crystal of claim 1 to a warm-blooded animal or human having sepsis.

5. A method of treating sepsis, comprising administering the pharmaceutical composition of claim 2 to a warm-blooded animal or human having sepsis.

* * * * *